(12) United States Patent
Ozaki et al.

(10) Patent No.: US 8,708,893 B2
(45) Date of Patent: Apr. 29, 2014

(54) STRUCTURAL UNIT, ENDOSCOPE, AND ADHERING METHOD

(75) Inventors: Takao Ozaki, Saitama (JP); Toshiaki Fukunaga, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 418 days.

(21) Appl. No.: 12/711,896

(22) Filed: Feb. 24, 2010

(65) Prior Publication Data

US 2010/0228088 A1    Sep. 9, 2010

(30) Foreign Application Priority Data

Mar. 5, 2009   (JP) ................................ 2009-051697

(51) Int. Cl.
*A61B 1/04*    (2006.01)
(52) U.S. Cl.
USPC ........................................................ 600/130
(58) Field of Classification Search
USPC ................................................. 600/130, 140
See application file for complete search history.

(56) References Cited

U.S. PATENT DOCUMENTS

| | | | |
|---|---|---|---|
| 5,380,320 A | | 1/1995 | Morris |
| 5,876,331 A | * | 3/1999 | Wu et al. ........................ 600/139 |
| 6,083,152 A | * | 7/2000 | Strong ............................ 600/139 |
| 6,547,721 B1 | | 4/2003 | Higuma et al. |
| 2005/0288545 A1 | | 12/2005 | Matsumoto et al. |
| 2006/0018080 A1 | * | 1/2006 | Schnetker ................... 361/301.5 |
| 2007/0088200 A1 | | 4/2007 | Dahmen et al. |
| 2008/0088701 A1 | | 4/2008 | Unsai et al. |
| 2008/0114205 A1 | | 5/2008 | Kagawa et al. |

FOREIGN PATENT DOCUMENTS

| | | |
|---|---|---|
| EP | 0978251 A1 | 2/2000 |
| JP | 2570405 | 5/1998 |
| JP | 2000-51142 A | 2/2000 |
| JP | 2001-46323 A | 2/2001 |
| JP | 2001046323 A * | 2/2001 |
| JP | 2004-000681 A | 1/2004 |
| JP | 3826137 B2 | 9/2006 |
| JP | 4590046 B2 | 12/2010 |

OTHER PUBLICATIONS

English translation of JP2001-046323.*
European Search Report dated Jun. 22, 2010.
Japanese Office Action dated Dec. 11, 2012 with partial English translation thereof.
European Office Action dated Nov. 19, 2013.

* cited by examiner

*Primary Examiner* — Clayton E Laballe
*Assistant Examiner* — Linda B Smith
(74) *Attorney, Agent, or Firm* — McGinn IP Law Group, PLLC

(57) ABSTRACT

The present invention provides a structural unit, an endoscope and an adhering method that suppress deterioration in adhesive strength of an adhesive that adheres plural structural members that structure the endoscope. An imaging unit 68 side of an adhesive 88 is covered by a first moisture-proof coating 91, and an obverse side of the adhesive 88 is covered by a second moisture-proof coating 92. Due thereto, in autoclave sterilization processing or the like, even if moisture passes along a wire portion 86 and penetrates into the imaging unit 68, penetration of the moisture into the adhesive is suppressed by the first moisture-proof coating 91. Due thereto, deterioration in adhesive strength of the adhesive, that adheres plural structural members of the imaging unit 68, can be suppressed.

20 Claims, 7 Drawing Sheets

STRUCTURAL UNIT, ENDOSCOPE, AND ADHERING METHOD

CROSS-REFERENCE TO RELATED APPLICATION

This application claims priority under 35 USC 119 from Japanese Patent Application No. 2009-051697, filed Mar. 5, 2009, the disclosure of which is incorporated by reference herein.

BACKGROUND

1. Technical Field

The present invention relates to a structural unit, an endoscope, and an adhering method.

2. Related Art

An endoscope for medical care observes organs and the like by an insertion portion thereof being inserted into a body cavity, and carries out various types of medical treatments by using treatment instruments that are inserted within a treatment instrument insert-through channel of the endoscope. Therefore, when an endoscope that has been used once is to be reused on another patient, in order to prevent infection between patients via the endoscope, the endoscope must be disinfected/sterilized after the examination or treatment ends. For disinfecting and sterilization, there are methods that use an autoclave or the like that is a sterilizer that uses a disinfecting liquid, ethylene oxide gas, formalin gas, hydrogen peroxide gas plasma, ozone, or high-temperature high-pressure water vapor.

An autoclave that sterilizes endoscopes by high-temperature high-pressure steam is a method of disinfecting and sterilizing that has conventionally become popular widely around the world. This method has the many advantages such as having good reliability of the sterilizing effect, not having residual toxicity, having a low running cost, and the like. Exemplary conditions at the time of carrying out high-pressure steam sterilization on an endoscope are a sterilization process at 132° C. for 4 minutes in a pre-vacuum type, and a sterilization process at 132° C. for 10 minutes in a gravity type, as stipulated in the US standard ANSI/AAMI S37-1992 that is approved by the American National Standards Institute and published by the Association for the Advancement of Medical Instrumentation. Under these conditions, there is the problem that damage to the medical instrument is great.

Examples of damage that autoclave sterilization treatment causes to endoscopes are clouding of the optical system and deterioration or breakage of electrical parts and wires at the periphery of the imaging element that are due to steam entering into the imaging unit that includes the imaging element at the distal end portion of the endoscope, and deterioration of the electrical parts and wires due to moisture entering into the substrate or switches within the endoscope.

As a countermeasure to these problems, Japanese Patent Application Laid-Open (JP-A) No. 2000-51142 discloses a structure in which outer surfaces, other than the front surface of a first lens 16, are covered by a steam-impermeable ceramic coating film 45 so as to prevent steam from entering into the imaging unit.

However, in the structure of JP-A No. 2000-51142, moisture passes along wires and the like and penetrates into the inner side of the coating film, and the adhesive strength of the adhesive at the inner side of the coating film deteriorates.

SUMMARY

In view of the above, the present invention provides a structural unit, an endoscope, and an adhering method that suppress deterioration of the adhesive strength of an adhesive that adheres plural structural members that structure an endoscope.

An aspect of the present invention is a structural unit that structures a portion of an endoscope and that includes: plural structural members that structure a portion of the structural unit; a first moisture-proof layer that is moisture-proof and is formed on a surface of at least one of the plural structural members; and an adhesive that is coated on a surface of the first moisture-proof layer, and adheres the plural structural members.

BRIEF DESCRIPTION OF THE DRAWINGS

An exemplary embodiment of the present invention will be described in detail based on the following figures, wherein.

DETAILED DESCRIPTION

Figure 1:
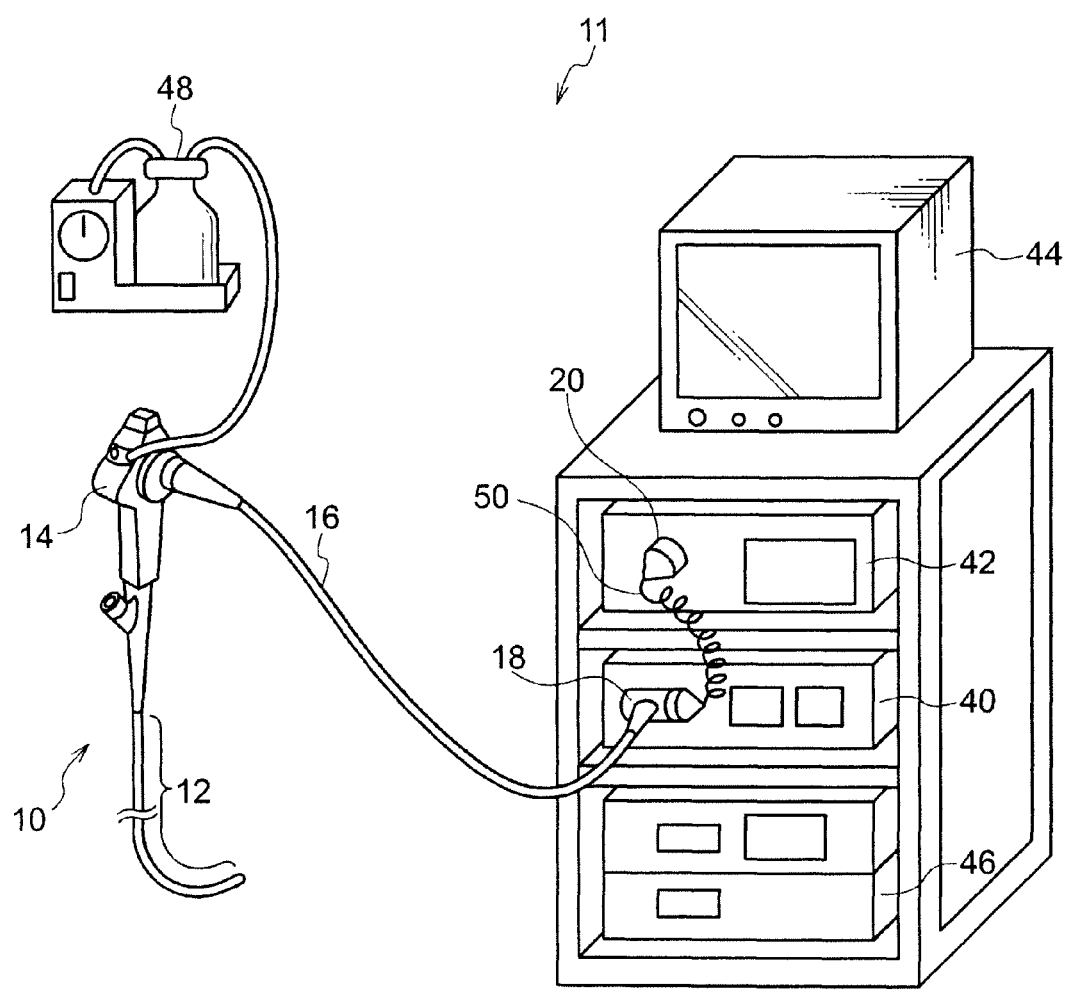
FIG. 1 is a drawing showing the overall structure of an endoscope system 11 relating to an exemplary embodiment.
Figure 2:
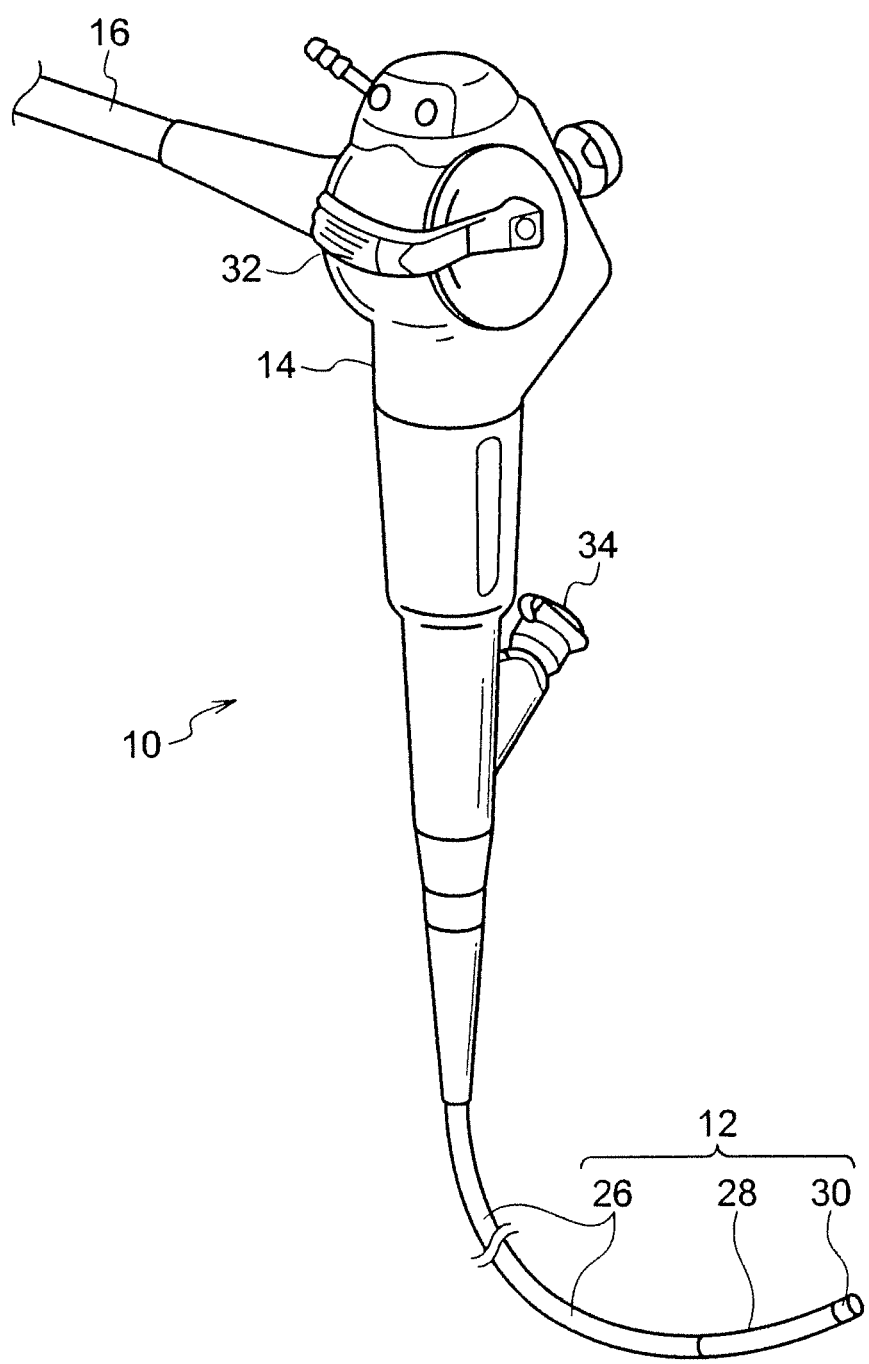
FIG. 2 is a drawing showing the structure of an endoscope 10 relating to the exemplary embodiment.

Hereinafter, an example of an exemplary embodiment relating to the present invention will be described on the basis of the drawings. First, the overall structure of an endoscope system 11 relating to the present exemplary embodiment will be described. FIG. 1 is a drawing showing the overall structure of the endoscope system 11 relating to the present exemplary embodiment. FIG. 2 is a drawing showing the structure of an endoscope 10 relating to the present exemplary embodiment.

As shown in FIG. 1, the endoscope system 11 relating to the present exemplary embodiment has: an endoscope 10 that has an imaging unit 68 (see FIG. 3 and FIG. 4) that image-captures an observed region, and a portion of which is inserted in a body cavity; a light source unit section 40 to which the endoscope 10 is connected so as to be freely detachable, and that supplies illumination light to the endoscope 10; an image processing section 42 that processes images (video images and still images) captured by the imaging unit 68 of the endoscope 10; a display section 44 that displays images that have been processed at the image processing section 42; a data storage section 46 that stores images that have been processed at the image processing section 42; and a suction device 48 that sucks air and various types of fluids from within the body cavity through the endoscope 10.

The endoscope 10 is structured to include plural structural units that structure a portion of the endoscope 10. Specifically, as shown in FIG. 1 and FIG. 2, the endoscope 10 is structured to include: an insertion portion 12 that is elongated and flexible and is inserted into a body cavity of a patient; an operation portion 14 provided at the proximal end side of the insertion portion 12; a universal cord 16 that is flexible and extends from the side portion of the operation portion 14; a connector portion 18 that is provided at an end portion of the universal cord 16 and can be freely detachably connected to the light source unit section 40; and an electric connector portion 20 to which a signal cable 50, that extends from the side portion of the connector portion 18 and can be connected to the image processing section 42, can be freely detachably connected.

As shown in FIG. 2, the insertion portion 12 is structured to include: a flexible tube portion 26 that is flexible; a bending portion 28 that is provided at the distal end side of the flexible tube portion 26 and can bend due to operation of the operation portion 14; and a distal end portion 30 that is provided at the distal end of the insertion portion 12 and at which the imaging unit 68 that serves as an imaging means, and the like, are disposed.

A bending operation knob 32 for carrying out bending operation of the bending portion 28, and a treatment instrument insertion opening 34, that is an opening that communicates with an instrument insert-through channel 64 for inserting-through a treatment instrument disposed at the insertion portion 12, are provided at the operation portion 14.

Note that, at the endoscope 10, the bending portion 28 is structured so as to bend in two directions that are up and down. However, the bending portion 28 may be structured so as to bend in four directions that are up, down, left and right.

Mouthpieces such as a gas supply mouthpiece, that is freely detachably connected to a gas supply source (not shown) that is incorporated in the light source unit section 40 and is for supplying pressurized air, an injection mouthpiece, that is connected to an unillustrated water feeding means for feeding water from the distal end portion 30, and the like are provided at the connector portion 18.

The endoscope 10 is structured such that, after being used for observation or treatment, sterilization can be carried out thereon by high-temperature high-pressure steam sterilization (hereinafter called autoclave sterilization) after washing.

The processings of autoclave sterilization are the processes of, after the endoscopic diagnosis and treatment operation, carrying out pre-cleaning, and, after the pre-cleaning, carrying out a disinfecting or sterilizing operation, and storing the endoscope with the degree of cleanliness thereof maintained.

Exemplary conditions of autoclave sterilization are a sterilization process at 132° C. for 4 minutes in a pre-vacuum type, and a sterilization process at 132° C. for 10 minutes in a gravity type, as stipulated in the US standard ANSI/AAMI S37-1992 that is approved by the American National Standards Institute and published by the Association for the Advancement of Medical Instrumentation.

When the sterilization operation is carried out, the endoscope must be stored in a form in which the sterility is ensured, such as, for example, being stored in a sterilization case that is hermetically sealed, being sealed in a sterilization bag, or the like. The sterilization operation itself also is carried out in a form that takes into consideration the storage after the sterilization operation, such as the sterilization treatment is carried out while the endoscope is sealed in a sterilization bag, or the like.

Figure 3:
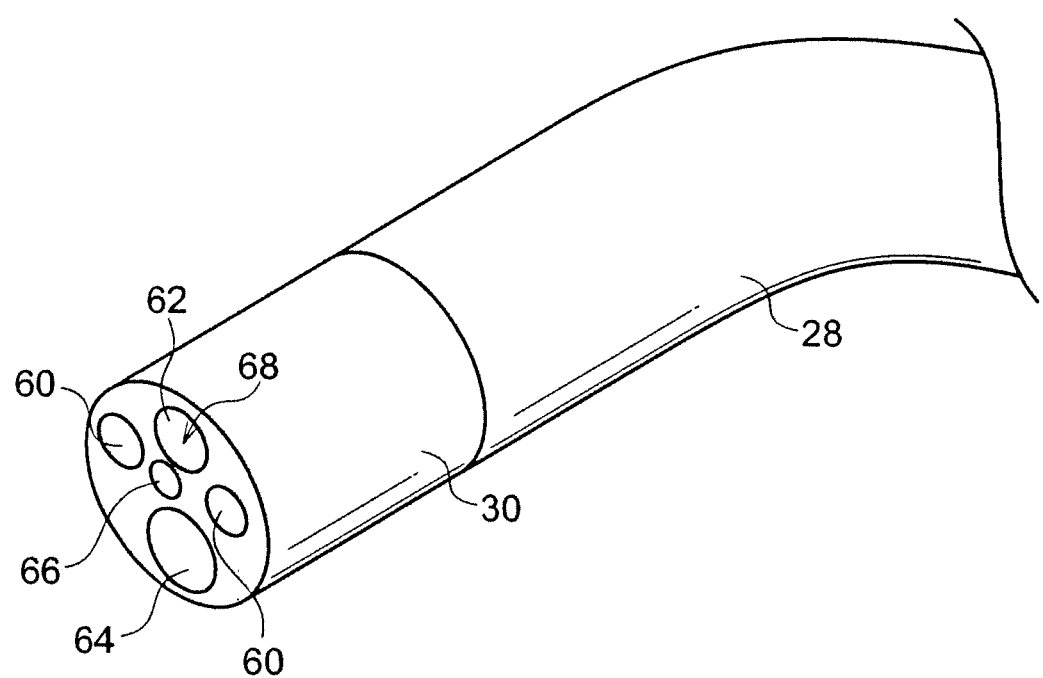
FIG. 3 is a schematic drawing showing the structure of a distal end portion of an insertion portion relating to the exemplary embodiment.
Figure 4:
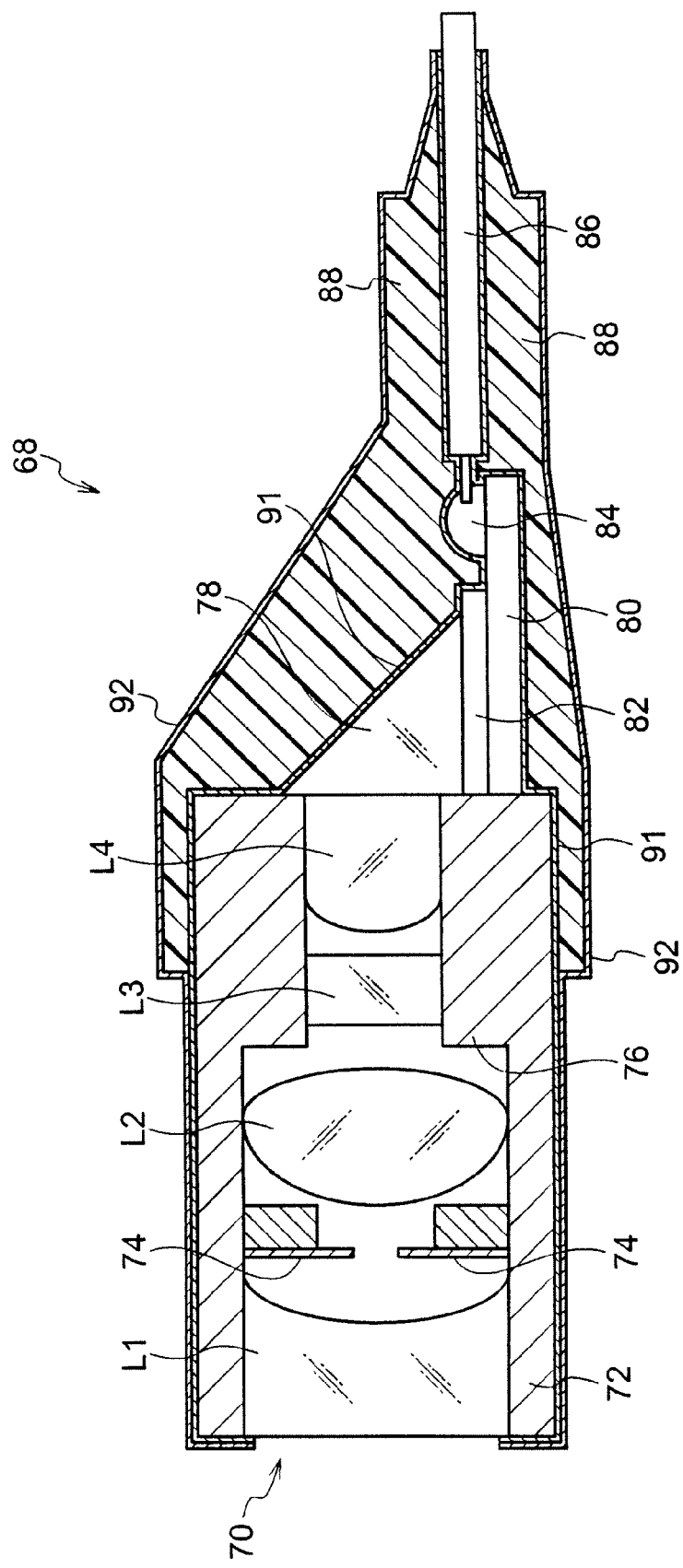
FIG. 4 is a schematic drawing showing the structure of an imaging unit relating to the exemplary embodiment.

(Structure of Distal End Portion 30 of Insertion Portion 12)
Next, the structure of the distal end portion 30 of the insertion portion 12 will be described. FIG. 3 is a schematic drawing showing the structure of the distal end portion 30 of the insertion portion 12. FIG. 4 is a schematic drawing showing the structure of the imaging unit 68.

As shown in FIG. 3, the distal end portion 30 of the insertion portion 12 has: an illumination window 60 from which the illumination light from the illuminating optical system exits; the imaging unit 68 (see FIG. 4) that is an example of a structural unit that structures a portion of the endoscope; an observation window 62 that structures the imaging unit 68; the instrument insert-through channel 64 for inserting-through a treatment instrument; and a nozzle 66 that jets-out fluid for cleaning (e.g., cleaning water or pressurized air) toward the observation window 62 when the observation window 62 is soiled.

As shown in FIG. 4, the imaging unit 68 is structured to include plural structural members that structure a portion of the imaging unit 68. Specifically, the imaging unit 68 has an observation optical system 70 in which a first lens L1, a second lens L2, a third lens L3 and a fourth lens L4 are arranged in that order from the object side, and a lens barrel 72 to which the observation optical system 70 is mounted.

The first lens L1 is a planoconcave lens whose object side is planar and whose imaging side is a concave surface. The planar side thereof is exposed at the observation window 62. Further, the second lens L2, that is positioned further toward the imaging side than the first lens L1, is a planoconvex lens whose convex surface is directed toward the object side. Moreover, the third lens L3 is a planoconcave lens whose concave surface is directed toward the imaging side, and the fourth lens L4 is a convex lens.

A spacing member 74, whose outer peripheral side portion is formed from an annular plate of a predetermined width and that has the function of blocking harmful light, is provided between the first lens L1 and the second lens L2.

A prism 78, for bending the optical axis of the objective optical system by 90°, is joined and fixed to the imaging side end surface of the lens barrel 72. Further, an imaging element (CCD) 82, that serves as an imaging means and is mounted to a substrate 80, is joined to the prism 78. A wire portion 86 is connected by solder 84 to the substrate 80.

A first moisture-proof coating 91 serving as a first moisture-proof layer is formed on the obverse (the outer surface that is exposed to the outer side) of the imaging unit 68. Specifically, the first moisture-proof coating 91 that is moisture-proof is formed on the obverses (the outer surfaces that are exposed to the outer side) of the lens barrel 72, the prism 78, the substrate 80, the imaging element (CCD) 82, the solder 84 and the wire portion 86.

For example, a polyparaxylylene resin is used as the first moisture-proof coating 91. Examples of polyparaxylylene resins are polymonochloroparaxylylene, polyparaxylylene, polydichloroparaxylylene, and the like. Polyparaxylylene resins whose respective qualities are suitable can be selected or combined so as to form a coating agent.

Specifically, for example, PARYLENE C (manufactured by Parylene Japan) is used as the polyparaxylylene resin.

The first moisture-proof coating 91 is formed by chemical vapor depositing polyparaxylylene resin for example.

The coated thickness of the polyparaxylylene resin is preferably around 5 to 80 μm. If the thickness is less than 5 μm, the moisture-proof effect is not exhibited. If the thickness exceeds 80 μm, the flexibility of the first moisture-proof coating 91 cannot be ensured.

When chemical vapor deposition is used, the coated thickness of the first moisture-proof coating 91 can be adjusted by the time that the imaging unit 68 is left within the resin atmosphere.

Note that it suffices to form the first moisture-proof coating 91 on at least one of the structural members that structure the imaging unit 68.

An adhesive 88 that adheres the respective portions of the imaging unit 68 is formed on the obverse (the outer surface exposed to the outer side) of the first moisture-proof coating 91. For example, an epoxy adhesive is used as the adhesive 88.

A second moisture-proof coating 92 that is moisture-proof is formed on the obverse (the outer surface exposed to the outer side) of the adhesive 88.

Due thereto, the imaging unit 68 side of the adhesive 88 is covered by the first moisture-proof coating 91, and the obverse side is covered by the second moisture-proof coating 92. Namely, the adhesive 88 is in a state of being enveloped by the first moisture-proof coating 91 and the second moisture-proof coating 92.

Owing to this structure, during autoclave sterilization processing and the like, even if moisture passes along the wire portion 86 and penetrates into the imaging unit 68, penetration of this moisture into the adhesive is suppressed by the first moisture-proof coating 91.

During autoclave sterilization processing and the like, even if moisture exists at the obverse side of the adhesive, penetration of this moisture into the adhesive is suppressed by the second moisture-proof coating 92.

Due thereto, deterioration of the adhesive strength of the adhesive, that adheres plural structural members of the imaging unit 68, can be suppressed.

Note that there may be a structure in which the second moisture-proof coating 92 is not formed.

In the same way as the first moisture-proof coating 91, for example, a polyparaxylylene resin is used as the second moisture-proof coating 92. The second moisture-proof coating 92 can be made to be the same structure as the first moisture-proof coating 91.

Note that the first moisture-proof coating 91 and the second moisture-proof coating 92 may be the same material, or different materials may be used therefor.

For example, the first moisture-proof coating 91 must be coated on fine portions of the fine wire portion. Therefore, a coating material whose permeability into narrow gaps is more than that of the second moisture-proof coating 92 may be used. For the second moisture-proof coating 92, qualities as a protective film rather than coating onto complex portions is prioritized, and a coating material having better heat resistance than the first moisture-proof coating 91 may be used.

Accordingly, the first moisture-proof coating 91 is formed of PARYLENE C (manufactured by Parylene Japan), whereas the second moisture-proof coating 92 may be formed of the same PARYLENE C (manufactured by Parylene Japan) as the first moisture-proof coating 91, or may be PARYLENE HT (manufactured by Parylene Japan) that is more heat-resistant than PARYLENE C, or diamond like carbon (DLC), a ceramic coating, or the like.

The adhering method at the imaging unit 68 will be described next.

First, in a first step, the first moisture-proof coating 91 that is moisture-proof is formed on the surfaces of the plural structural members (the lens barrel 72, the prism 78, the substrate 80, the imaging element (CCD) 82, the solder 84 and the wire portion 86) of the imaging unit 68 that structures a portion of the endoscope 10.

The first moisture-proof coating 91 is formed by chemical vapor depositing a polyparaxylylene resin.

The chemical vapor deposition is carried out by, for example, placing the imaging unit 68 within a chamber of a chemical vapor deposition device and reducing the pressure, and thereafter, feeding vaporized polyparaxylylene into the chamber, and leaving the imaging unit 68 within that atmosphere for a predetermined time period.

Next, in a second step that is carried out after the first step, the adhesive 88 is coated on the surface of the first moisture-proof coating 91, and adheres the plural structural members. This adhesive 88 seals, adheres and fixes the substrate 80 and other electrical parts and the wire portion 86.

Next, in a third step that is carried out after the second step, the second moisture-proof layer that is moisture-proof is formed on the surface of the adhesive 88.

The second moisture-proof coating 92 is formed by chemical vapor depositing a polyparaxylylene resin.

In the same way as the first moisture-proof coating 91, the chemical vapor deposition is carried out by, for example, placing the imaging unit 68 within a chamber of a chemical vapor deposition device and reducing the pressure, and thereafter, feeding vaporized polyparaxylylene into the chamber, and leaving the imaging unit 68 within that atmosphere for a predetermined time period.

The structural unit that structures a portion of the endoscope 10 is not limited to the imaging unit 68, and may be a unit that is structured from plural structural members. The above-described adhering structure (sealing structure) can be applied to other structural units.

The structural units may be, for example, the flexible tube portion 26, the connector portion 18, a push button device 124 disposed at the operation portion 14, or the like. As will be described hereinafter, the above-described adhering structure (sealing structure) can be applied thereto.

Further, the above-described adhering structure (sealing structure) can be applied at the connection portions where electrically-conductive members, such as wires or the like, are electrically connected to one another.

(Flexible Tube Portion 26)

Figure 5:
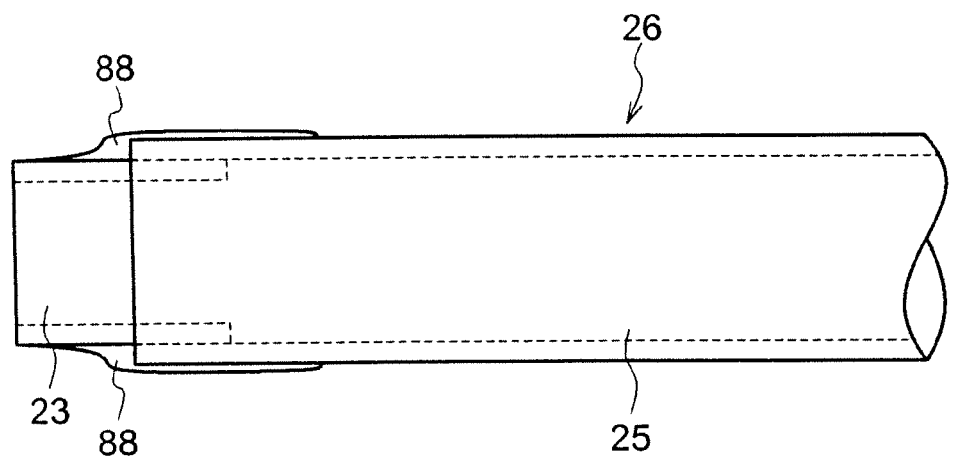
FIG. 5 is a schematic drawing showing an example in which an adhering structure (sealing structure) relating to the exemplary embodiment is applied to a flexible tube portion.

As shown in FIG. 5, the flexible tube portion 26 is structured to have, at a longitudinal direction end portion thereof, a tubular body 23 that is elongated and is formed of metal for example, and an outer skin 25 that is made of resin and formed at the outer periphery of the tubular body 23.

Figure 6:
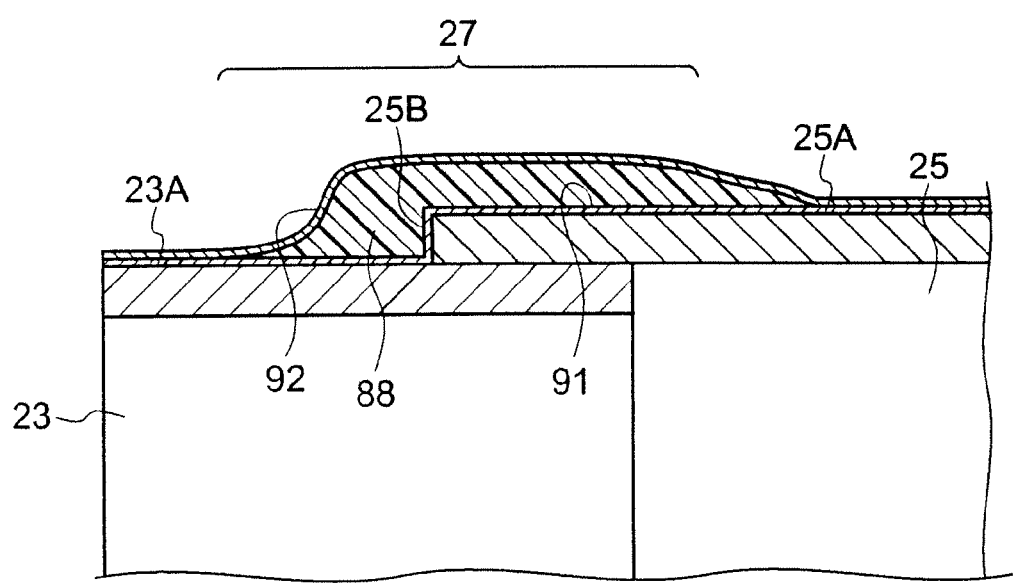
FIG. 6 is an enlarged drawing showing, in an enlarged manner, an adhesion region at the flexible tube portion shown in FIG. 5.

The tubular body 23 projects from the outer skin 25 in the longitudinal direction. As shown in FIG. 6, a step portion 27 that is step-shaped is formed by an outer peripheral surface 25A and an end surface 25B of the outer skin 25, and an outer peripheral surface 23A of the tubular body 23.

At the step portion 27, the first moisture-proof coating 91 is formed on the obverse (the outer surface exposed to the outer side) of the step portion 27. Specifically, the first moisture-proof coating 91 is formed on the outer peripheral surface 25A and the end surface 25B of the outer skin 25, and the outer peripheral surface 25A of the tubular body 23.

The adhesive 88, that adheres the respective portions of the flexible tube portion 26, is formed on the obverse (the outer surface exposed to the outer side) of the first moisture-proof coating 91.

The second moisture-proof coating 92 that is moisture-proof is formed on the obverse (the outer surface exposed to the outer side) of the adhesive 88.

(Connector Portion 18)

Figure 7:
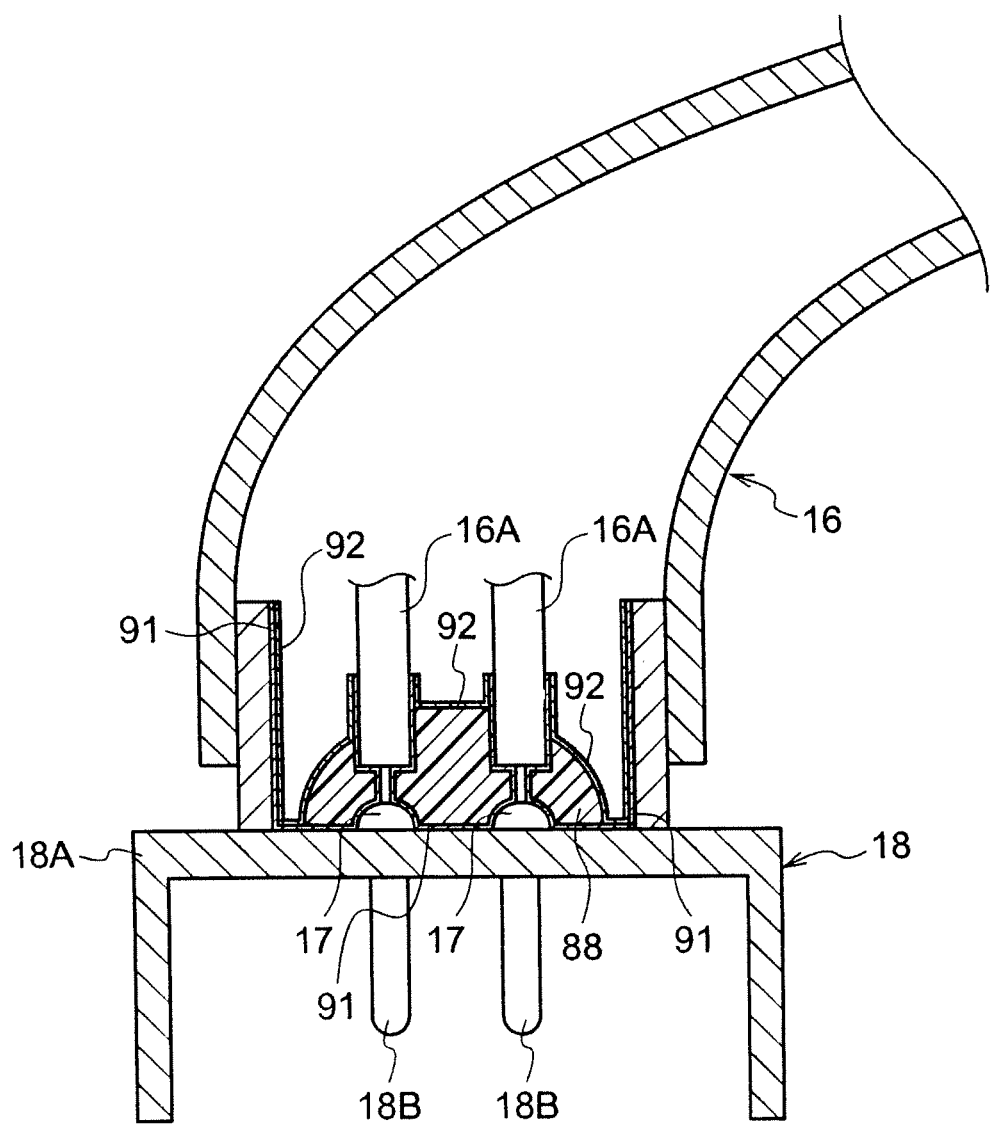
FIG. 7 is a schematic drawing showing an example in which the adhering structure (sealing structure) relating to the exemplary embodiment is applied to a connector portion.

As shown in FIG. 7, the connector portion 18 has a housing 18A that is fixed to the distal end portion of the universal cord 16, and connector pins 18B that are electrically connected to the light source unit section 40.

Wire portions 16A of the universal cord 16 are electrically connected to the connector pins 18B by solder 17.

The first moisture-proof coating 91 is formed on the obverse (the outer surface exposed to the outer side) of the connection portion where the wire portions 16A and the connector pins 18B are connected by the solder 17. Specifically, the first moisture-proof coating 91 is formed on the end portions of the wire portions 16A, the solder 17, and the end portions of the connector pins 18B.

The adhesive 88, that adheres the end portions of the wire portions 16A, the solder 17, and the end portions of the connector pins 18B, is formed on the obverse (the outer surface exposed to the outer side) of the first moisture-proof coating 91.

The second moisture-proof coating 92 that is moisture-proof is formed on the obverse (the outer surface exposed to the outer side) of the adhesive 88.

(Push Button Device 124)

Figure 8:
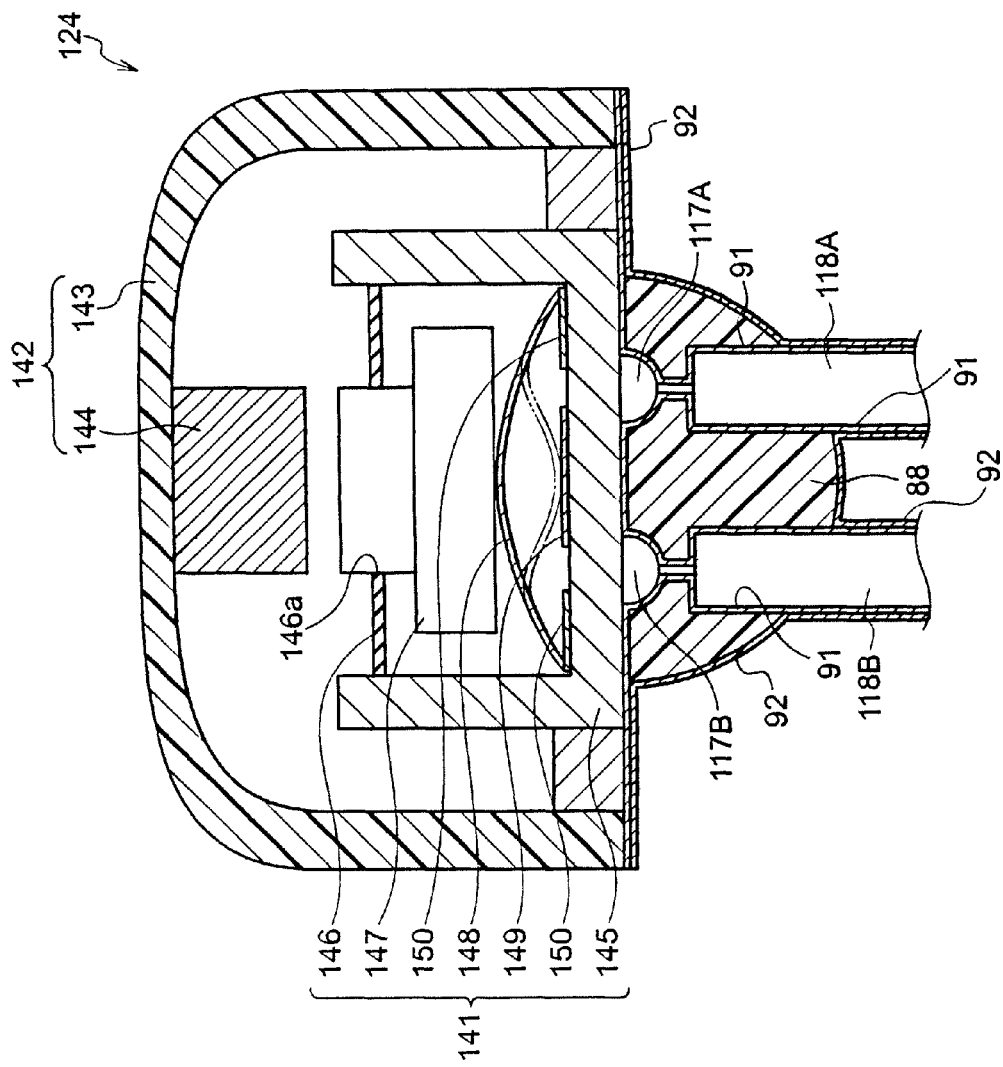
FIG. 8 is a drawing showing an example in which the adhering structure (sealing structure) relating to the exemplary embodiment is applied to a push-button device.

As shown in FIG. 8, the push button device 124 is structured to include a switch 141 that enables high-temperature high-pressure steam sterilization, and a push member 142. The push member 142 is an operation member that watertightly covers the switch 141 and can be displaced with respect to the switch 141 by elastic deformation.

The push member 142 is structured from a waterproof film portion 143 that is watertightly fixed to the outer package of the operation portion 14 and that can deform elastically when directly touched by an operator, and a push portion 144 that is fixed to the waterproof film portion 143 and is disposed so as to face the switch 141 and can push the switch 141.

The switch 141 has: an accommodating body 145 having an opening that is disposed so as to face the push portion 144; a holding cap 146 that watertightly covers the opening portion of the accommodating body 145 and has a holding opening portion 146a that is disposed so as to face the push portion 144; and a stem 147 that is displaceable and is held so as to slide freely at the holding opening portion 146a of the holding cap 146. Further, at the switch 141, a deforming contact 148 serving as a movable contact, a first fixed contact 150, and a second fixed contact 149 are incorporated within the accommodating body 145.

The first fixed contact 150 is formed in an annular shape in plan view, and is electrically connected to the end portion of the deforming contact 148.

The deforming contact 148 is a member at which a portion thereof or the entirety thereof elastically deforms. The deforming contact 148 is formed of metal, is formed in a dome shape, is disposed such that the convex portion of the dome faces the stem 147, and the dome end portion is fixed or tightly held at the inner side wall of the accommodating body 145 or the like. Due to this structure, the push member 142 is operated and the stem 147 is pushed and displaced, and as a result, the central portion of the deforming contact 148 flexes due to elastic deformation in accordance with the pushing force caused by displacement of the stem 147, and can contact the second fixed contact 149, as shown by the two-dot chain line in FIG. 8. On the other hand, when the pushing force is released, the deforming contact 148 can return to its original form as shown by the solid line in FIG. 8, due to the restoring force that the deforming contact 148 itself has. The second fixed contact 149 is fixed to the floor portion within the accommodating body 145, and is disposed so as to be able to contact the deforming contact 148 in a flexed state where the waterproof film portion 143 is pushed.

Due to the deforming contact 148 and the second fixed contact 149 contacting one another and returning to the state of non-contact, the electrically on/off state of the switch 141 is switched.

Here, the first fixed contact 150 is electrically connected to a wire portion 118A by solder 117A. The second fixed contact 149 is electrically connected to a wire portion 118B by solder 117B.

The first moisture-proof coating 91 is formed on the obverse (the outer surface exposed to the outer side) of the connection portion where the wire portion 118A and the first fixed contact 150 are connected by the solder 117A, and on the obverse (the outer surface exposed to the outer side) of the connection portion where the wire portion 118B and the second fixed contact 149 are connected by the solder 117B. Specifically, the first moisture-proof coating 91 is formed on the end portion of the wire portion 118A, the end portion of the wire portion 118B, the solder 117A and the solder 117B.

The adhesive 88, that adheres the end portion of the wire portion 118A, the end portion of the wire portion 118B, the solder 117A and the solder 117B, is formed on the obverse (the outer surface exposed to the outer side) of the first moisture-proof coating 91.

The second moisture-proof coating 92 that is moisture-proof is formed on the obverse (the outer surface exposed to the outer side) of the adhesive 88.

As described above, the first moisture-proof layer that is moisture-proof is formed on the surface of at least one of plural structural members. An adhesive, that adheres the plural structural members, is coated on the surface of the first moisture-proof layer. Due thereto, the first moisture-proof layer is disposed between the structural members and the adhesive.

In autoclave sterilizing processing or the like, even if moisture passes along the structural members and penetrates into the structural unit, the penetration of this moisture into the adhesive is suppressed by the first moisture-proof layer, and further, by the second moisture-proof layer. Due thereto, a deterioration in the adhesive strength of the adhesive that adheres the plural structural members can be suppressed.

The first moisture-proof layer and the second moisture-proof layer are coatings formed by chemical vapor deposition of a paraxylylene resin. Because paraxylylene resins generally are materials having an excellent moisture-proof quality, the penetration of moisture into the adhesive is effectively suppressed by the first moisture-proof layer. Due thereto, a deterioration in the adhesive strength of the adhesive that adheres the plural structural members can be suppressed.

Further, the first moisture-proof layer is a coating whose permeability into the gaps of the structural members is more than that of the second moisture-proof layer. The first moisture-proof layer can be formed to as far as the fine portions of the structural members. The moisture-proof effect with respect to the adhesive is thereby improved.

The present invention is not limited to the above-described exemplary embodiment, and various modifications, changes, and improvements can be made thereto.

What is claimed is:

1. A structural unit that structures a portion of an endoscope, the structural unit comprising:
   a plurality of structural members that structure a portion of the structural unit;
   a first moisture-proof layer that is moisture-proof and is formed on a surface of at least one of the plurality of structural members;
   an adhesive that is coated on a surface of the first moisture-proof layer, and adheres the plurality of structural members, and
   a second moisture-proof layer that is moisture-proof and is formed on a surface of the adhesive, wherein the adhesive is in a state of being enveloped by the first moisture-proof layer and the second moisture-proof layer, end portions of the first moisture-proof layer and end portions of the second moisture-proof layer being joined together.

2. The structural unit of claim 1, wherein the first moisture-proof layer comprises a coating formed by a chemical vapor deposition of a paraxylylene resin.

3. The structural unit of claim 1, wherein a permeability of the first moisture-proof layer into gaps of the structural members is more than that of the second moisture-proof layer.

4. The structural unit of claim 1, wherein the second moisture-proof layer comprises a coating formed by chemical vapor deposition of a paraxylylene resin.

5. The structural unit of claim 1, wherein the first moisture-proof layer and the second moisture-proof layer encircle the adhesive.

6. The structural unit of claim 1, wherein the first moisture-proof layer and the second moisture-proof layer encircle an entirety of the adhesive.

7. The structural unit of claim 1, wherein the first moisture-proof layer and the second moisture-proof layer are disposed on an entirety of side surfaces of the adhesive.

8. The structural unit of claim 1, wherein the end portions of the first moisture-proof layer are disposed on surfaces of the end portions of the second moisture-proof layer.

9. The structural unit of claim 1, wherein the adhesive is located outside an area of the structural unit that the end portions of the first moisture-proof layer abut the end portions of the second moisture-proof layer.

10. An endoscope, comprising:
a plurality of structural members that structure a portion of the endoscope;
a first moisture-proof layer that is moisture-proof and is formed on a surface of at least one of the plurality of structural members;
an adhesive that is coated on a surface of the first moisture-proof layer, and adheres the plurality of structural members; and
a second moisture-proof layer that is moisture-proof and is formed on a surface of the adhesive,
wherein the adhesive is in a state of being enveloped by the first moisture-proof layer and the second moisture-proof layer, end portions of the first moisture-proof layer and end portions of the second moisture-proof layer being joined together.

11. The endoscope of claim 10, wherein the first moisture-proof layer comprises a coating formed by a chemical vapor deposition of a paraxylylene resin.

12. The endoscope of claim 10, wherein a permeability of the first moisture-proof layer into gaps of the structural members is more than that of the second moisture-proof layer.

13. The endoscope of claim 10, wherein the second moisture-proof layer comprises a coating formed by chemical vapor deposition of a paraxylylene resin.

14. The endoscope of claim 10, wherein the end portions of the first moisture-proof layer are disposed on surfaces of the end portions of the second moisture-proof layer.

15. The endoscope of claim 10, wherein the adhesive is located outside an area of the endoscope that the end portions of the first moisture-proof layer abut the end portions of the second moisture-proof layer.

16. An adhering method, comprising:
forming a first moisture-proof layer, that is moisture-proof, on a surface of at least one of a plurality of structural members of a structural unit that structures a portion of an endoscope;
after the forming of the first moisture-proof layer, coating an adhesive on a surface of the first moisture-proof layer, and adhering the plurality of structural members; and
after the coating of the adhesive, forming a second moisture-proof layer, that is moisture-proof, on a surface of the adhesive,
wherein the adhesive is in a state of being enveloped by the first moisture-proof layer and the second moisture-proof layer, end portions of the first moisture-proof layer and end portions of the second moisture-proof layer being joined together.

17. The adhering method of claim 16, wherein the forming of the first moisture-proof layer includes a coating by a chemical vapor deposition of a paraxylylene resin.

18. The adhering method of claim 16, wherein a permeability of the first moisture-proof layer into gaps of the structural members is more than that of the second moisture-proof layer.

19. The adhering method of claim 16, wherein the coating of the adhesive includes a coating by a chemical vapor deposition of a paraxylylene resin.

20. The adhering method of claim 16, wherein the end portions of the first moisture-proof layer are disposed on surfaces of the end portions of the second moisture-proof layer such that the adhesive is located outside an area that the end portions of the first moisture-proof layer abut the end portions of the second moisture-proof layer.

* * * * *